(12) United States Patent
Kim et al.

(10) Patent No.: US 8,398,963 B2
(45) Date of Patent: *Mar. 19, 2013

(54) COSMETIC AGENT

(75) Inventors: Son Nguyen Kim, Hemsbach (DE); Claudia Wood, Weinheim (DE)

(73) Assignee: BASF SE, Ludwigshafen (DE)

( * ) Notice: Subject to any disclaimer, the term of this patent is extended or adjusted under 35 U.S.C. 154(b) by 858 days.

This patent is subject to a terminal disclaimer.

(21) Appl. No.: 10/204,346

(22) PCT Filed: Feb. 22, 2001

(86) PCT No.: PCT/EP01/02047
§ 371 (c)(1),
(2), (4) Date: Aug. 20, 2002

(87) PCT Pub. No.: WO01/62809
PCT Pub. Date: Aug. 30, 2001

(65) Prior Publication Data
US 2003/0147929 A1    Aug. 7, 2003

(30) Foreign Application Priority Data
Feb. 23, 2000 (DE) .................................. 100 08 263

(51) Int. Cl.
*A61K 31/74* (2006.01)
*A61K 8/00* (2006.01)
(52) U.S. Cl. .............. 424/78.02; 424/70.1; 424/401
(58) Field of Classification Search .................. 424/401, 424/70.1, 78.02; 514/772, 772.4
See application file for complete search history.

(56) References Cited

U.S. PATENT DOCUMENTS

| | | | |
|---|---|---|---|
| 3,914,403 A | 10/1975 | Valan | |
| 4,767,613 A * | 8/1988 | Nuber et al. | 424/47 |
| 5,132,417 A | 7/1992 | Potthoff-Karl | |
| 5,278,269 A | 1/1994 | Mita | |
| 5,306,484 A | 4/1994 | Potthoff-Karl | |
| 5,635,169 A * | 6/1997 | Blankenburg et al. | 424/70.15 |
| 5,663,261 A | 9/1997 | Hori | |
| 5,997,855 A * | 12/1999 | Liu | 424/78.24 |
| 6,123,933 A * | 9/2000 | Hayama et al. | 424/69 |
| 6,132,705 A * | 10/2000 | Schehlmann et al. | 424/78.02 |
| 6,329,472 B1 * | 12/2001 | Kim et al. | 525/326.9 |
| 6,403,074 B1 * | 6/2002 | Blankenburg et al. | 424/70.12 |
| 6,489,397 B2 * | 12/2002 | Kim et al. | 525/127 |
| 6,524,564 B1 * | 2/2003 | Kim et al. | 424/70.12 |
| 6,579,517 B1 | 6/2003 | Kim et al. | |
| 6,737,049 B1 * | 5/2004 | Kim et al. | 424/70.1 |
| 7,459,148 B2 * | 12/2008 | Nguyen-Kim et al. | 424/70.11 |
| 7,829,070 B2 * | 11/2010 | Nguyen-Kim et al. | 424/70.16 |

FOREIGN PATENT DOCUMENTS

| | | |
|---|---|---|
| CA | 2040963 | 10/1991 |
| DE | 198 21 732 A1 | 11/1999 |
| EP | 0 815 839 | 1/1998 |
| EP | 0 957 119 A1 | 11/1999 |
| EP | 1 002 811 | 5/2000 |
| JP | 04-225912 | 8/1992 |
| JP | 10-265352 | 10/1998 |
| JP | 2001-048755 | 2/2001 |
| WO | 96/19966 | 7/1996 |
| WO | 96/19967 | 7/1996 |
| WO | 96/19971 | 7/1996 |
| WO | 96/20227 | 7/1996 |
| WO | 96/20694 | 7/1996 |
| WO | WO 99/04750 | 2/1999 |
| WO | 99/58100 | 11/1999 |
| WO | WO 00/11051 | 3/2000 |

OTHER PUBLICATIONS

Derwent Abst. 94-342 756, Nov. 3, 1994.
Derwent Abst. 2000-207031/19, Aug. 24, 1998.
English language abstract of document JP 10-265352.
English language abstract and partial translation of document JP 2001-048755.

* cited by examiner

*Primary Examiner* — Lakshmi Channavajjala
(74) *Attorney, Agent, or Firm* — Novak Druce Connolly Bove + Quigg LLP

(57) ABSTRACT

The present invention relates to a cosmetic composition containing at least one water-soluble or water-dispersible polymer which has, in incorporated form, a) 5 to 50% by weight of an α,β-ethylenically unsaturated monomer of the formula I

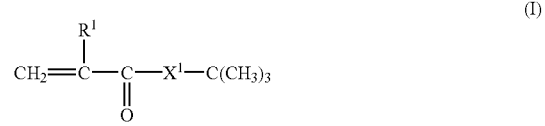

where $R^1$ and $X^1$ are defined herein, b) 25 to 90% by weight an N-vinylamide and/or N-vinyllactam, c) 0.5 to 30% by weight of a compound having a free-radically polymerizable, α,β-ethylenically unsaturated double bond and a cationogenic and/or cationic group per molecule, and d) 0 to 30% by weight of an α,β-ethylenically unsaturated monomer of the formula II

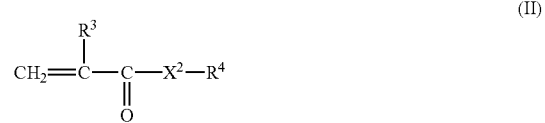

where $R^3$, $X^2$, and $R^4$ are defined herein, and the salts thereof.

26 Claims, No Drawings

COSMETIC AGENT

The present invention relates to a cosmetic composition which comprises, in copolymerized form, at least one water-soluble or water-dispersible polymer.

In cosmetics, polymers with film-forming properties are used for setting, styling and improving the structure of hair. These hair-treatment compositions generally comprise a solution of the film former in an alcohol or a mixture of alcohol and water.

Hair-setting compositions are generally sprayed onto the hair in the form of aqueous-alcoholic solutions. After the solvent has evaporated, the hair is held in the desired shape at the mutual points of contact by the polymer which remains. The polymers should firstly be hydrophilic so that they can be washed out of the hair, but secondly should be hydrophobic so that the hair treated with the polymers retains its shape even when atmospheric humidity is high and does not stick together. In order to achieve as efficient a hair-setting action as possible, it is furthermore desirable to use polymers which have a relatively high molecular weight and a relatively high glass transition temperature (at least 15° C.).

Another current demand on hair-treatment compositions is that they should achieve a good setting action, even when used by people who have hair which is by its very nature particularly strong and/or dark. In this connection, as natural as possible an appearance and shine should be imparted to the hair.

A disadvantage of many known hair-setting polymers is the so-called "flaking" effect, i.e. after combing, a white, flaky residue remains on the hair. This is generally considered by users to be extremely unpleasant. The "flaking" effect is particularly evident in people with a dark hair color and/or particularly thick hair. The possibility of using hair-setting formulations which have this effect is thus considerably impaired in particular in the Asian market. Regarded as possible causes of the "flaking" effect are, inter alia, the chemical structure of the hair-setting polymers used and, in particular, the particle size of the spray.

In addition to the abovementioned properties, hair-setting polymers should therefore preferably have high propellant gas compatibility in order to permit formulation in spray cans under the highest possible pressure. This is true both for classical propellants based on propane/butane, and also for their replacements, e.g. those based on dimethyl ether.

It is known to use copolymers based on monomers containing cationic or cationogenic groups in hair-treatment compositions. For example, U.S. Pat. Nos. 3,914,403 and 3,954,960 describe hair cosmetics which comprise copolymers comprising, in incorporated form, N-vinylpyrrolidone, a monomer having a quaternizable group, and optionally further monomers.

WO-A-96/19966 and WO-A-96/20227 describe hair-treatment compositions based on terpolymers which comprise, in incorporated form, a vinyllactam, an acrylate or acrylamide having a quaternary amino group and a further hydrophobic monomer, preferably a $C_4$- to $C_{32}$-alkyl (meth)acrylate or -(meth)acrylamide. The propane/butane compatibility of the polymers used in these compositions is still in need of improvement.

WO-A-96/19967 describes a process for the preparation of copolymers from vinylpyrrolidone and N-3,3-dimethylaminopropylmethacrylamide and the use thereof in hair-treatment compositions. WO-A-96/19971 describes hairspray formulations having a low content of volatile organic compounds (VOC content) which comprise a terpolymer of vinylpyrrolidone, vinylcaprolactam and N-3,3-dimethylaminopropylmethacrylamide (DMAPMA). WO-A-96/20694 describes a hairspray formulation having a low VOC content which comprises a tetramer of vinylpyrrolidone, vinylcaprolactam, DMAPMA and a $C_8$- to $C_{18}$-alkylacrylamide or acrylate. Polymers which comprise a higher proportion of long-chain acrylate and/or acrylamide monomers in incorporated form generally lead to very soft films. Hair-treatment compositions which comprise such polymers are generally in need of improvement with regard to their setting action.

A disadvantage of the abovementioned compositions based on polymers having a high vinyllactam content is that they are tacky and readily decline with regard to setting action when atmospheric humidity is high. None of the above-mentioned documents describes the use of polymers which comprise, in incorporated form, at least one tert-butyl ester or an N-tert-butylamide of an α,β-ethylenically unsaturated carboxylic acid, in hair cosmetics.

EP-A-0 372 546 and EP-A-0 728 778 describe film-former resins which comprise, in copolymerized form, at least one (meth)acrylamide, at least one $C_1$- to $C_4$-alkyl (meth)acrylate, at least one N,N-dialkyl (meth)acrylate or N,N-dialkyl (meth)acrylamide and optionally at least one hydroxyalkyl (meth)acrylate or polyalkylene glycol (meth)acrylate. These copolymers have only poor solubility in ethanol, and the resulting films are hard, meaning that when they are used in hair-setting compositions, they do not impart a natural appearance to the hair. Their propane-butane compatibility is also in need of improvement. A disadvantage of using copolymers which comprise, in incorporated form, hydroxyalkyl (meth)acrylates and/or polyalkylene glycol (meth)acrylates is also the high viscosity and the tackiness of aqueous preparations based thereon.

Anionic polymers having propane/butane compatibility are already known, including polymers based on tert-butyl acrylate and tert-butyl methacrylate.

EP-A-379 082 describes, for example, a hair-setting composition comprising, as film former, a copolymer which comprises, in copolymerized form, A) 75 to 99% by weight of tert-butyl (meth)acrylate, B) 1 to 25% by weight of (meth)acrylic acid and C) 0 to 10% by weight of a further free-radically copolymerizable hydrophobic monomer.

Hair-setting compositions based on these copolymers which comprise only components A) and B) make the hair too hard and have too poor a propane/butane compatibility. Copolymers which additionally comprise a monomer C) are in need of improvement with regard to their ability to be washed off.

DE-A-43 14 305, like EP-A-379 082, describes a hair-setting polymer based on tert-butyl (meth)acrylate and (meth) acrylic acid which comprises, in copolymerized form, 0 to 60% by weight of a $C_1$- to $C_{18}$-alkyl (meth)acrylate or a mixture thereof with N—$C_1$— to —$C_{18}$-alkyl(meth)acrylamides. Although additional monomers with a carbon number of more than 8 lead under some circumstances to a better propane/butane compatibility, the ability to be washed off is considerably impaired at the same time.

A disadvantage of anionic polymers is also that the hair-treatment compositions based thereon frequently have the above-described "flaking" effect.

German Patent Application DE-A-198 38 196 describes cationic polymers obtainable by free-radical copolymerization of (a) 50 to 70% by weight of one or more monomers of the formula I

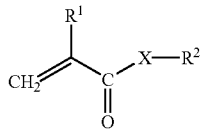

(I)

X=O, NR$^1$,
R$^1$=H, C$_1$-C$_8$-alkyl,
R$^2$=tert-butyl, (b) 5 to 45% by weight of one or more monomers of the formula II

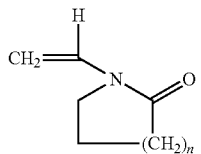

(II)

where n=1 to 3, (c) 5 to 40% by weight of a monoethylenically unsaturated monomer having at least one amine-containing group, where up to 20% by weight, based on (a), (b) and (c), of the monomer (a) can be replaced by a monomer of the formula I where R$^2$=C$_8$-C$_{22}$-alkyl, and the use of such polymers in hair cosmetics.

It is an object of the present invention to provide novel compositions, in particular hair-treatment compositions, which have high propellant compatibility and/or essentially do not exhibit a "flaking" effect. Preferably, these compositions should have a good setting action and impart smoothness and suppleness to the hair. They should generally have good ability to be washed out.

We have found that this object is achieved by cosmetic compositions which comprise at least one water-soluble or water-dispersible polymer which comprises, in copolymerized form, at most 50% by weight of at least one tert-butyl ester and/or N-tert-butylamide of an α,β-ethylenically unsaturated carboxylic acid.

The present invention therefore relates to a cosmetic composition comprising at least one water-soluble or water-dispersible polymer which comprises, in incorporated form, a) 5 to 50% by weight of at least one α,β-ethylenically unsaturated monomer of the formula I

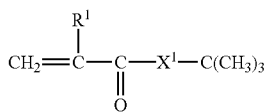

(I)

in which
R$^1$ is hydrogen or C$_1$- to C$_8$-alkyl, and
X$^1$ is O or NR$^2$, where R$^2$ is hydrogen, C$_1$- to C$_8$-alkyl or C$_5$-to C$_8$-cycloalkyl, b) 25 to 90% by weight of at least one N-vinylamide and/or N-vinyllactam, c) 0.5 to 30% by weight of at least one compound having a free-radically polymerizable, α,β-ethylenically unsaturated double bond and at least one cationogenic and/or cationic group per molecule, d) 0 to 30% by weight of at least one α,β-ethylenically unsaturated monomer of the formula II

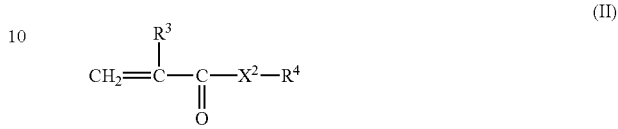

(II)

in which
R$^3$ is hydrogen or C$_1$- to C$_8$-alkyl,
X$^2$ is O or NR$^5$, where R$^5$ is hydrogen C$_1$- to C$_8$-alkyl or C$_5$-to C$_8$-cycloalkyl, and
R$^4$ is hydrogen or a linear C$_1$- to C$_{22}$-alkyl radical, and the salts thereof. Unless stated otherwise, the data given here and below is in % by weight, based on the total amount of all components forming the polymer, i.e. the sum of all parts by weight of monomers a), b), c), d) and optionally other copolymerized components is 100% by weight.

For the purposes of the present invention, the expression C$_1$- to C$_8$-'alkyl' includes straight-chain and branched alkyl groups having 1 to 8 C atoms. They are preferably straight-chain or branched C$_1$-C$_6$-alkyl and particularly preferably C$_1$-C$_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

The C$_5$- to C$_8$-cycloalkyl group is, for example, cyclopentyl, cyclohexyl, cycloheptyl or cyclooctyl.

Compounds which can be derived from acrylic acid and methacrylic acid are referred to below in partially abbreviated form by adding the syllable "(meth)" to the compound derived from acrylic acid.

Component a)

Component a) is preferably an α,β-ethylenically unsaturated compound of the formula I, in which
R$^1$ is hydrogen, methyl or ethyl, and
X$^1$ is O or NR$^2$, where R$^2$ is hydrogen, methyl, ethyl, n-propyl, isopropyl, n-butyl, sec-butyl, tert-butyl or cyclohexyl.
In particular, R$^2$ is hydrogen.

It is also possible to use mixures of compounds of component a).

Component a) is preferably tert-butyl acrylate, tert-butyl methacrylate, tert-butyl ethacrylate, N-tert-butylacrylamide, N-tert-butylmethacrylamide, N-tert-butylethacrylamide and mixtures thereof.

Component b)

Suitable monomers b) are N-vinyllactams and derivatives thereof which can, for example, have one or more C$_1$-C$_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6- ethyl-2-piperidone, N-vinyl-7-methyl-2-caprolactam, N-vinyl-7-ethyl-2-caprolactam etc.

Suitable monomers b) are also N-vinylamides, such as N-vinylformamide, N-vinylacetamide, N-vinylpropionamide, N-vinyl-n-butyramide, N-vinyl-tert-butyramide, etc. Preference is given to using N-vinylformamide.

Component b) is preferably chosen from vinylpyrrolidone, vinylcaprolactam, vinylformamide and mixtures thereof.

Component c)

The cationogenic and/or cationic groups of component c) are preferably nitrogen-containing groups, such as primary, secondary and tertiary amino groups, and quaternary ammonium groups. The nitrogen-containing groups are preferably tertiary amino groups or quaternary ammonium groups. Charged cationic groups can be produced from the amine nitrogen either by protonation, e.g. with carboxylic acids, such as lactic acid, or mineral acids, such as phosphoric acid, sulfuric acid and hydrochloric acid, or by quaternization, e.g. using alkylating agents such as $C_1$- to $C_4$-alkyl halides or sulfates. Examples of such alkylating agents are ethyl chloride, ethyl bromide, methyl chloride, methyl bromide, dimethyl sulfate and diethyl sulfate.

Suitable compounds c) are, for example, the esters of α,β-ethylenically unsaturated mono- and dicarboxylic acids with $C_2$- to $C_{12}$-aminoalcohols which have been $C_1$- to $C_8$-dialkylated on the amine nitrogen. Suitable acid components of these esters are, for example, acryl acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof. N,N-Dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminocyclohexyl (meth)acrylate etc. are preferred. Preference is given to using N,N-dimethylaminoethyl (meth)acrylate and N,N-dimethylaminopropyl (meth)acrylate.

Suitable monomers c) are also the amides of the abovementioned α,β-ethylenically unsaturated mono- and dicarboxylic acids with diamines which have a tertiary and a primary or secondary amino group. Examples thereof include N-[2-(dimethylamino)ethyl]acrylamide,
N-[2-(dimethylamino)ethyl]methacrylamide,
N-[3-(dimethylamino)propyl]acrylamide,
N-[3-(dimethylamino)propyl]methacrylamide,
N-[4-(dimethylamino)butyl]acrylamide,
N-[4-(dimethylamino)butyl]methacrylamide,
N-[2-(diethylamino)ethyl]acrylamide,
N-[4-(dimethylamino)cyclohexyl]acrylamide,
N-[4-(dimethylamino)cyclohexyl]methacrylamide etc. Preference is given to using N-[3-(dimethyl-amino)propyl] acrylamide,
N-[3-(dimethylamino)propyl]methacrylamide.

Suitable monomers c) are also N,N-diallyl-N-alkylamines and acid addition salts and quaternization products thereof. Alkyl here is preferably $C_1$-$C_{24}$-alkyl. Preference is given to N,N-diallyl-N-methylamine and N,N-diallyl-N,N-dimethylammonium compounds, such as, for example, the chlorides and bromides.

Suitable monomers c) are also vinyl- and allyl-substituted nitrogen heterocycles, such as N-vinylimidazole, N-vinyl-2-methylimidazole, 2- and 4-vinylpyridine, 2- and 4-allylpyridine etc.

Component d)

Component d) is preferably chosen from compounds of the formula II

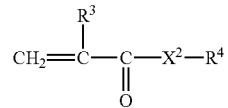

(II)

in which
$R^3$ is hydrogen or $C_1$- to $C_4$-alkyl,
$R^4$ is hydrogen or a straight-chain $C_1$- to $C_{30}$-alkyl radical, and
$X^2$ is O or $NR^5$, where $R^5$ is hydrogen, $C_1$- to $C_8$-alkyl or $C_5$- to $C_8$-cycloalkyl.

In the formula II, $R^3$ is preferably hydrogen, methyl or ethyl.

$X^2$ is preferably O or NH.

$R^4$ is preferably hydrogen, methyl, ethyl, n-propyl, n-butyl, n-pentyl, n-hexyl, n-heptyl, n-octyl, undecyl, lauryl, tridecyl, myristyl, pentadecyl, palmityl, margarinyl, stearyl, palmitoleinyl, oleyl or linolyl.

Component d) is preferably chosen from n-butyl (meth)acrylate, n-octyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth)acrylate, arachidyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl (meth)acrylate, linolenyl (meth)acrylate, stearyl (meth)acrylate, lauryl (meth)acrylate, n-octyl(meth)acrylamide, n-nonyl(meth)acrylamide, n-decyl(meth)acrylamide, n-undecyl(meth)acrylamide, tridecyl(meth)acrylamide, myristyl(meth)acrylamide, pentadecyl(meth)acrylamide, palmityl(meth)acrylamide, heptadecyl(meth)acrylamide, nonadecyl(meth)acrylamide, arachidyl(meth)acrylamide, behenyl(meth)acrylamide, lignocerenyl(meth)acrylamide, cerotinyl(meth)acrylamide, melissinyl(meth)acrylamide, palmitoleinyl (meth)acrylamide, oleyl(meth)acrylamide, linolyl(meth)acrylamide, linolenyl(meth)acrylamide, stearyl(meth)acrylamide, lauryl(meth)acrylamide and mixtures thereof.

Preferred as component d) are also compounds of the formula II in which
$R^3$ is hydrogen, methyl or ethyl,
$X^2$ is O or NH, and
$R^4$ is hydrogen, and where $X^2$=O, also salts thereof.

Preferred compounds d) are primary amides of α,β-ethylenically unsaturated monocarboxylic acids, such as acrylamide, methacrylamide, ethacrylamide etc.

Particularly preferred compounds d) are compounds of the formula II where $X^2$=O and $R^4$=H, such as acrylic acid, methacrylic acid, ethacrylic acid, and alkali metal salts thereof, e.g. the sodium and potassium salts thereof, and mixtures thereof. The use of these compounds d) which contain acid groups results in polymers containing anionogenic groups, which can be partially or completely converted to anionic groups by neutralization, as described below. The monomers d) may of course also be already present in salt form.

The abovementioned compounds of component d) can be used individually or in the form of mixtures.

In a preferred embodiment, component d) comprises at least one compound of the formula II where $X^2$=O and $R^4$=H in an amount of from 0.1 to 20% by weight, and preferably in an amount of from 0.2 to 10% by weight, based on the total amount of monomers a), b), c) and d). Of these, preference is given to the monomers acrylic acid and methacrylic acid. As well as the monomers of the formula II where $X^2$=O and $R^4$=H, component d) can of course also comprise monomers which are different therefrom ($R^4 \neq H$, if $X^2$=O).

The polymers used in the composition according to the invention can comprise, in copolymerized form, at least one further component chosen from e) compounds different from d) having a free-radically polymerizable α,β-ethylenically unsaturated double bond and at least one anionogenic and/or anionic group per molecule, f) monomers having a crosslinking action and at least two ethylenically unsaturated nonconjugated double bonds, g) free-radically polymerizable monomers different from a) to f), and mixtures thereof.

The water-soluble or water-dispersible polymers used in the cosmetic compositions according to the invention can, in addition to the abovementioned monomer components, also comprise, in copolymerized form, component e) which is chosen from compounds which are different from d) and which have a free-radically polymerizable, α,β-ethylenically unsaturated double bond and at least one anionogenic and/or anionic group per molecule and mixtures thereof.

The anionogenic and anionic groups of the compounds of component e) are preferably chosen from carboxylate and/or sulfonate groups and salts thereof obtainable by partial or complete neutralization with a base.

Suitable compounds e) are, for example, ethylenically unsaturated mono- and/or dicarboxylic acids and half-esters and anhydrides thereof, such as fumaric acid, maleic acid, itaconic acid, crotonic acid, maleic anhydride, monobutyl maleate etc. and alkali metal salts thereof, such as sodium and potassium salts thereof.

Suitable monomers e) are also acrylamidoalkanesulfonic acids and salts thereof, such as 2-acrylamido-2-methylpropanesulfonic acid and alkali metal salts thereof, e.g. sodium and potassium salts thereof.

The water-soluble or water-dispersible polymers comprise the compounds of components d) and e) containing at least one anionogenic and/or anionic group per molecule preferably in an amount of from 0 to 15% by weight, preferably 0.1 to 12% by weight, based on the total weight of the monomers to be polymerized, in copolymerized form.

The polymers used in the compositions according to the invention may also comprise, in copolymerized form, at least one crosslinking monomer f) which is different from the compounds of component a) to e) and which has at least two α,β-ethylenically unsaturated double bonds per molecule.

The compositions according to the invention comprise the component f) preferably in an amount of from 0.001 to 4% by weight, in particular 0.01 to 2% by weight, based on the total amount of all components forming the polymer.

Suitable crosslinkers f) are, for example, acrylates, methacrylates, allyl ethers or vinyl ethers of at least dihydric alcohols. The OH groups of the parent alcohols may here be entirely or partially etherified or esterified; however, the crosslinkers comprise at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic neopentyl glcyol monoester, 2,2-bis(4-hydroxyphenyl)propane, 2,2-bis[4-(2-hydroxypropyl)-phenyl]propane, diethylene glycol, triethylene glycol, tetraethylene glycol, dipropylene glycol, tripropylene glycol, tetrapropylene glycol, 3-thiopentane-1,5-diol and polyethylene glycols, polypropylene glycols and polytetrahydrofurans with molecular weights of in each case 200 to 10000. Apart from the homopolymers of ethylene oxide or propylene oxide, it is also possible to use block copolymers of ethylene oxide or propylene oxide or copolymers which contain ethylene oxide and propylene oxide groups in incorporated form. Examples of parent alcohols having more than 2 OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. The polyhydric alcohols can of course also be used following reaction with ethylene oxide or propylene oxide, as the corresponding ethoxylates or propoxylates, respectively. The polyhydric alcohols can also firstly be converted into the corresponding glycidyl ethers by reaction with epichlorohydrin.

Further suitable crosslinkers f) are the vinyl esters or the esters of monohydric, unsaturated alcohols with ethylenically unsaturated $C_3$- to $C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, the monohydric, unsaturated alcohols can also be esterified with polybasic carboxylic acids, for example malonic acid, tartaric acid, trimellitic acid, phthalic acid, terephthalic acid, citric acid or succinic acid.

Further suitable crosslinkers are esters of unsaturated carboxylic acids with the above-described polyhydric alcohols, for example oleic acid, crotonic acid, cinnamic acid or 10-undecenoic acid.

Suitable as monomers (f) are also straight-chain or branched, linear or cyclic, aliphatic or aromatic hydrocarbons which have at least two double bonds, which in the case of aliphatic hydrocarbons must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20,000.

Also suitable as crosslinkers are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Also suitable are the amides of allylamine and unsaturated carboxylic acids, such as acrylic acid, methacrylic acid, itaconic acid, maleic acid, or at least dibasic carboxylic acids, as have been described above.

Triallylamine and triallylmonoalkylammonium salts, e.g. triallylmethylammonium chloride or methylsulfate, are also suitable as crosslinkers.

Suitable crosslinkers are also N-vinyl compounds of urea derivatives, at least difunctional amides, cyanurates or urethanes, for example of urea, ethyleneurea, propyleneurea or tartramide, e.g. N,N'-divinylethyleneurea or N,N'-divinylpropyleneurea.

Suitable crosslinkers are also the urethane acrylates mentioned in DE-A-19838852.

Further suitable crosslinkers are divinyldioxane, tetraallylsilane or tetravinylsilane.

Preference is given to crosslinkers which are soluble in the monomer mixture.

Preferred crosslinkers are, for example, pentaerythritol triallyl ether, methylenebisacrylamide, triallylamine and triallylalkylammonium salts, divinylimidazole, N,N'-divinylethyleneurea, reaction products of polyhydric alcohols with acrylic acid or methacrylic acid, methacrylates and acrylates of polyalkylene oxides or polyhydric alcohols which have been reacted with ethylene oxide and/or propylene oxide and/or epichlorohydrin.

The monomers f) can in each case be used individually or in a mixture with other monomers from the same group.

The use of at least one crosslinking compound f) generally leads to polymers with a higher molecular weight than corresponding polymers obtained in the absence of component f). Polymers which comprise, in copolymerized form, at least one compound of component f) are preferably suitable for cosmetic compositions in the form of a shampoo, hair foam or hair gel.

The polymers used in the compositions according to the invention can also comprise, in copolymerized form, at least one further free-radically polymerizable monomer g) which is different from the compounds of components a) to f).

The compositions according to the invention comprise the component g) preferably in an amount of from 0.1 to 10% by weight, in particular 0.5 to 5% by weight, based on the total amount of all components forming the polymer.

Suitable monomers g) are e.g. vinylaromatics, such as styrene, a-methylstyrene, o-chlorostyrene and vinyltoluenes, vinyl halides, such as vinyl chloride, vinylidene halides, such as vinylidene chloride, monoolefins, such as ethylene and propylene, nonaromatic hydrocarbons with at least two conjugated double bonds, such as butadiene, isoprene and chloroprene, and mixtures thereof.

The polymer preferably comprises
7 to 50% by weight, preferably 10 to 45% by weight, of at least one component a),
30 to 87% by weight, preferably 40 to 85% by weight, in particular 50 to 80% by weight, of at least one component b),
1 to 25% by weight, preferably 3 to 20% by weight, of at least one component c),
0 to 25% by weight, preferably 0.1 to 20% by weight, of at least one component d), where component d) comprises in particular 1 to 10% by weight of a compound II where $X^2$=O and $R^4$=H,
and, if desired,
0 to 15% by weight, preferably 0.1 to 12% by weight, of at least one component e),
in copolymerized form.

Preferably, during the preparation of the water-soluble or water-dispersible polymers according to the invention, the components c), d) and optionally e) are used in amounts such that the ratio of equivalents of cationogenic groups is greater than or equal to the equivalents of anionogenic groups.

Preference is given to polymers which comprise, in copolymerized form,
at least one compound of component a), chosen from tert-butyl acrlyate, tert-butyl methacrylate, N-tert-butylacrylamide, N-tert-butylmethacrylamide and mixtures thereof,
at least one compound of component b), chosen from N-vinylformamide, N-vinylpyrrolidone, N-vinylcaprolactam and mixtures thereof,
at least one component of component c), chosen from dimethylaminoethyl acrylate, dimethylaminoethyl methacrylate (DMAEMA), N-[3-(dimethylamino)propyl]acrylamide, N-[3-(dimethylamino)propyl]methacrylamide (DMAPMA) and mixtures thereof,
acrylic acid and/or acrylamide and/or methacrylic acid as compound of component d) and optionally one or more further compounds of component d), chosen from n-butyl acrylate, n-butyl methacrylate, n-stearyl acrylate, n-stearyl methacrylate, n-lauryl acrylate, n-lauryl methacrylate.

Particular preference is given to polymers which comprise, in copolymerized form, N-[3-(dimethylamino)propyl]methacrylamide and (meth)acrylic acid in the weight ratio 2:0.9 to 2:1.1.

In a preferred embodiment, the cosmetic compositions according to the invention additionally comprise at least one polysiloxane which contains polyalkylene oxide groups. The compositions can comprise these siloxanes in the form of a separate component and/or in incorporated form in one of the above-described water-soluble or water-dispersible polymers. The polysiloxanes are preferably incorporated by grafting, i.e. polymerizing the monomers a) to d) and optionally e) to g) in the presence of the polysiloxanes.

In a preferred embodiment of the invention, the water-soluble or water-dispersible polymers comprise, in incorporated form, a polysiloxane which contains polyalkylene oxide groups. The amount of polysiloxane is then preferably 1 to 20% by weight, based on the total amount of monomers a), b), c), d), optionally e) and polysiloxane. In this embodiment, the monomers d) preferably comprise at least one compound of the formula II where $X^2$=R and $R^4$=H, in particular acrylic acid and/or methacrylic acid or salts thereof in an amount of from 1 to 10% by weight, based on the total amount of components a), b), c), d), optionally e) and polysiloxane, and optionally other compounds of the formula II.

The polysiloxane is preferably chosen from compounds of the formula III

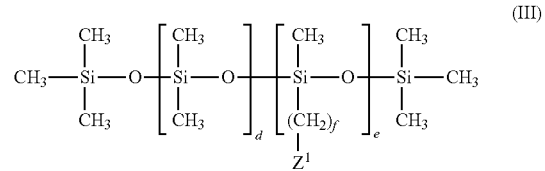

in which
the order of the siloxane units is arbitrary,
d and e, independently of one another are 0 to 100, where the sum d+e is at least 2,
f is an integer from 2 to 8,
$Z^1$ is a radical of the formula IV

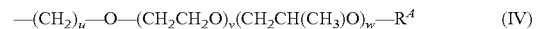

where
in the formula IV the order of the alkylene oxide units is arbitrary,
u is an integer from 1 to 8,
v and w, independently of one another, are an integer from 0 to 200, where the sum v+w is >0, and
$R^4$=H or $C_1$-$C_6$-alkyl, preferably H, $CH_3$ or $C_2H_5$.

The polysiloxanes preferably have a molecular weight in a range from about 300 to 30,000.

The total number of alkylene oxide units in the polysiloxanes, i.e. the sum v+w in the formula IV, is preferably in a range from about 3 to 200, preferably 5 to 180.

Suitable polysiloxanes are the compounds known under the international generic name dimethicone copolyols or as silicone surfactants, such as, for example, the compounds obtainable under the trade names Belsil® (Wacker) or Silvet® (Witco). Preference is given, for example, to Belsil® 6031 or Silvet®L.

The weight ratio of water-soluble or water-dispersible polymer to polysiloxane is preferably in a range from about 70:30 to 99.9:0.1, preferably about 85:15 to 99:1.

The invention further relates to a water-soluble or water-dispersible polymer which comprises, in copolymerized form, a) 5 to 50% by weight of at least one α,β-ethylenically unsaturated monomer of the formula I

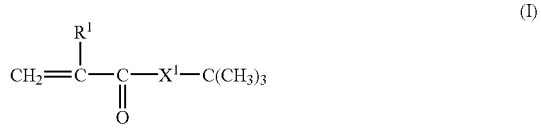

in which

R$^1$ is hydrogen or C$_1$- to C$_8$-alkyl, and

X$^1$ is O or NR$^2$, where R$^2$ is hydrogen, C$_1$- to C$_8$-alkyl or C$_5$- to C$_8$-cycloalkyl, b) 25 to 90% by weight of at least one N-vinylamide and/or N-vinyllactam, c) 0.5 to 30% by weight of at least one compound having a free-radically polymerizable, α,β-ethylenically unsaturated double bond and at least one cationogenic and/or cationic group per molecule, d) 0.1 to 30% by weight of at least one α,β-ethylenically unsaturated monomer of the formula II

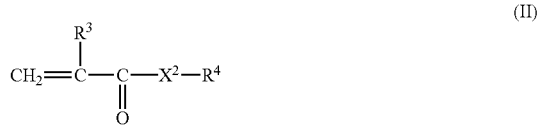

in which

R$^3$ is hydrogen or C$_1$- to C$_8$-alkyl,

X$^2$ is O or NR$^5$, in which R$^5$ is hydrogen C$_1$- to C$_8$-alkyl or C$_5$- to C$_8$-cycloalkyl, and R$^4$ is hydrogen or a linear C$_1$- to C$_{22}$-alkyl radical, With regard to the preferred monomers a), b), c) and d), the stated above also applies for the quantitative fractions of the monomers a), b), c) and d), based on the total amount of monomer.

The polymers according to the invention can also comprise, in copolymerized form, at least one further component chosen from e) compounds different from d) having a free-radically polymerizable α,β-ethylenically unsaturated double bond and at least one anionogenic and/or anionic group per molecule, f) monomers having a crosslinking action and at least two ethylenically unsaturated nonconjugated double bonds, g) free-radically polymerizable monomers different from a) to f), and mixtures thereof.

The component d) particularly preferably comprises at least one compound II where X$^2$=O and R$^4$=H, in particular acrylic acid and/or methacrylic acid, in an amount of from 0.1 to 20% by weight and, in particular, 1 to 10% by weight, based on the total amount of monomers a), b), c), d) and optionally further components. In addition, component d) can also comprise compounds of the formula II which are different therefrom (i.e. R$^4$≠H, if X$^2$=O), e.g. in an amount of from 0.1 to 25% by weight. The polymers according to the invention can of course also comprise, in copolymerized form, the abovementioned monomers of component e).

In a preferred embodiment, these polymers comprise at least one of the above-defined polysiloxanes in incorporated form, in particular one of the formula III. The amount of polysiloxane is then preferably 1 to 20% by weight, based on the total amount of monomers a), b), c) and d), optionally e) and polysiloxane. Such polymers generally comprise 1 to 10% by weight of at least one monomer d) of the formula II where X$^2$=O and R$^4$=H and optionally in addition further monomers of the formula II in copolymerized form, where the amount is likewise based on the total amount of a), b), c), d), optionally e) and polysiloxane.

Such polymers particularly preferably comprise the following in copolymerized form:

10 to 50% by weight of at least one monomer of the formula I (component a)), 25 to 70% by weight of at least one N-vinylamide and/or N-vinyl-lactam (component b)), 3 to 20% by weight of at least one of the monomers given under c), 1 to 10% by weight of at least one monomer of the formula II where X$^2$=O and R$^4$=H, 0 to 25% by weight of one or more monomers of the formula II where R$^4$≠H, if X$^2$=O and 1 to 20% by weight of at least one polysiloxane containing polyalkylene oxide groups, in particular a polysiloxane of the formula II, where all of the weight fractions given add up to 100% by weight.

The polymers used in the compositions according to the invention and the polymers according to the invention are prepared by free-radical polymerization by customary processes known to the person skilled in the art. These include free-radical bulk, emulsion, suspension and solution polymerization, preferably emulsion and solution polymerization. The amounts of compounds to be polymerized, based on solvents and dispersants, are generally chosen here such that about 30 to 80% by weight solutions, emulsions or dispersions are obtained. The polymerization temperature is generally from 30 to 120° C., preferably from 40 to 100° C.

The polymerization medium for the solution polymerization can consist either of only one organic solvent or of mixtures of water and at least one water-miscible, organic solvent. Preferred organic solvents are, for example, alcohols, such as methanol, ethanol, n-propanol, isopropanol, n-butanol, ketones, such as acetone and methyl ethyl ketone, tetrahydrofuran etc. If, for the polymerization, monomers d) and/or e) containing anionogenic and/or anionic groups, such as, for example, acrylic acid, methacrylic acid etc., are used, then the polymerization is preferably carried out in mixtures of water and at least one water-miscible organic solvent.

If monomers are used for the polymerization where component b) does not comprise N-vinylamides, then the pH can generally be varied during the polymerization within a wide range from weakly acidic through neutral to alkaline. If at least one N-vinylamide b) is used for the polymerization, then the pH of the reaction mixture, starting with the addition of this monomer, is preferably in a range from 6 to 8, in particular from 6.2 to 7.2.

The solution polymerization can be carried out either as a batch process or in the form of a feed process, including monomer feed, staged and gradient procedures. Preference is generally given to the feed process, in which, if desired, some of the polymerization mixture is introduced as an initial charge and heated to the polymerization temperature, and then the remainder of the polymerization mixture, usually by way of one or more spatially separate feeds, is fed to the polymerization zone continuously, in stages or under a concentration gradient, while the polymerization is maintained.

If, for the polymerization, monomers d) and/or e) containing anionogenic and/or anionic groups are used, then the addition thereof can take place together with the monomers containing cationogenic and/or cationic groups c) or temporally separate from these. The monomers containing anionogenic and/or anionic groups are preferably added when the addition of the monomers containing cationogenic and/or cationic groups is complete. If desired, the monomers containing anionogenic groups and, for example, acrylic acid, methacrylic acid etc., can also be added as neutralizing agents when polymerization has finished.

The initiators for the free-radical polymerization are customary peroxo or azo compounds. Examples thereof include dibenzoyl peroxide, tert-butyl perpivalate, tert-butyl per-2-ethylhexanoate, di-tert-butyl peroxide, 2,5-dimethyl-2,5-di (tert-butylperoxy)hexane, aliphatic or cycloaliphatic azo compounds, e.g. 2,2'-azobis(isobutyronitrile), 2,2'-azobis(2-methylbutyronitrile), 2,2'-azobis(2,4-dimethylvaleronitrile), 1,1'-azobis(1-cyclohexanecarbonitrile), 2-(carbamoylazo) isobutyronitrile, 4,4'-azobis(4-cyanovaleric acid) and the alkali metal and ammonium salts thereof, e.g. the sodium salt, dimethyl 2,2'-azobisisobutyrate, 2,2'-azobis[2-(2-imidazolin-2-yl)propane], 2,2'-azobis(2-amidinopropane) and the acid addition salts of the latter two compounds, e.g., the dihydrochlorides.

Also suitable as initiators are hydrogen peroxide, hydroperoxides in combination with reducing agents, and persalts. Suitable hydroperoxides are, for example, tert-butyl hydroperoxide, tert-amyl hydroperoxide, cumene hydroperoxide and pinane hydroperoxide, in each case in combination with, for example, a salt of hydroxymethanesulfinic acid, an iron (II) salt or ascorbic acid. Suitable persalts are, in particular, alkali metal peroxodisulfates.

The amount of initiator used, based on the monomers, is generally in a range of from about 0.1 to 2% by weight, based on the total weight of the monomers to be polymerized.

To achieve the desired K value of the polymers it is possible, particularly in the case of emulsion or suspension polymerization, to use a regulator. Suitable regulators are, for example, aldehydes, such as formaldehyde, acetaldehyde, propionaldehyde, n-butyraldehyde and isobutyraldehyde, formic acid, ammonium formate, hydroxylammonium sulfate and hydroxylammonium phosphate. It is also possible to use regulators which contain sulfur in organically bonded form, such as di-n-butyl sulfide, di-n-octyl sulfide, diphenyl sulfide etc., or regulators which contain sulfur in the form of SH groups, such as n-butyl mercaptan, n-hexyl mercaptan or n-dodecyl mercaptan. Also suitable are water-soluble, sulfur-containing polymerization regulators, such as, for example, hydrogen sulfites and disulfites. Further suitable regulators are allyl compounds, such as allyl alcohol or allyl bromide, benzyl compounds, such as benzyl chloride or alkyl halides, such as chloroform or tetrachloromethane.

If desired, following the polymerization reaction, one or more polymerization initiators are added to the polymer solution, and the polymer solution is heated, for example to the polymerization temperature or to temperatures above the polymerization temperature in order to complete the polymerization. Suitable initiators are the azo initiators mentioned above, and also all other customary initiators suitable for free-radical polymerization in aqueous solution, for example peroxides, hydroperoxides, peroxodisulfates, percarbonates, peroxo esters and hydrogen peroxide. These take the polymerization reaction to a higher conversion, such as, for example, 99.9%. The residual monomer content can alternatively also be reduced by acid hydrolysis. For this, the polymer solutions obtained by the above-described process are admixed with water and an acid, for example an organic acid, such as lactic acid, or a mineral acid, such as sulfuric acid, hydrochloric acid or phosphoric acid, and heated, preferably to temperatures $\leq 100°$ C., e.g. 50 to 100° C. The amount of acid is preferably chosen such that a pH in the range from 4.5 to 5.5 is reached. The heating is preferably in the form of steam distillation, steam-volatile residual monomers or hydrolysis products thereof, and optionally volatile solvents being removed. Preferably, a steam distillation is carried out until a head temperature of about 100° C. is reached.

The solutions forming in the polymerization can, where appropriate, be converted into solid powders by a prior art drying technique. Preferred techniques are, for example, spray drying, spray fluidized-bed drying, roller drying and belt drying. Freeze drying and freeze concentration can likewise be used. If desired, the solvent can also be removed, partially or completely, by customary methods, e.g. distillation under reduced pressure.

According to a preferred embodiment, the water-soluble or water-dispersible polymer used is a polymer which has been obtained by free-radical polymerization of the monomers forming the polymer in the presence of at least one polysiloxane which contains polyalkylene oxide groups.

The polymerization in the presence of at least one polysiloxane takes place by the processes described above, it being possible to use the polysiloxane component as a constituent of the initial charge, a monomer feed or as a separate feed.

The water-soluble or water-dispersible polymers used in the compositions according to the invention are cationic or cationogenic polymers. Charged cationic groups can be produced from the amine nitrogens of the cationogenic groups either by protonation, e.g. with carboxylic acids, such as lactic acid, or mineral acids, such as phosphoric acid, sulfuric acid and hydrochloric acid, or by quaternization, e.g. using alkylating agents, such as $C_1$- to $C_4$-alkyl halides or sulfates. This can be carried out either before the polymerization by appropriate reaction of the monomers, or after the polymerization. Depending on the intended use, neutralization can be partial, e.g. 5 to 95%, preferably 30 to 95%, or complete, i.e. 100%.

Polymers which additionally comprise, in copolymerized form, at least one compound of components d) and/or e) containing anionogenic groups can be partially or completely neutralized with a base. Bases which can be used for the neutralization of the polymers are alkali metal bases such as sodium hydroxide solution, potassium hydroxide solution, sodium carbonate, sodium hydrogencarbonate, potassium carbonate or potassium hydrogencarbonate, and alkaline earth metal bases such as calcium hydroxide, calcium oxide, magnesium hydroxide or magnesium carbonate, and ammonia and amines. Examples of suitable amines are $C_1$-$C_6$-alkylamines, preferably n-propylamine and n-butylamine, dialkylamines, preferably diethylpropylamine and dipropylmethylamine, trialkylamines, preferably triethylamine and triisopropylamine, $C_1$-$C_6$-alkyldiethanolamines, preferably methyl- or ethyldiethanolamine and di-$C_1$-$C_6$-alkylethanolamines and also glucamine and methylglucamine. Particularly for use in hair-treatment compositions, 2-amino-2-methyl-1-propanol, diethylaminopropylamine and triisopropanolamine have proven successful for the neutralization of the polymers containing acid groups. The neutralization of the polymers containing acid groups can also be carried out using mixtures of two or more bases, e.g. mixtures of sodium hydroxide solution and triisopropanolamine. Depending on the intended use, neutralization can be partial, e.g. 20 to 40%, or complete, i.e. 100%.

Polymers with ionogenic and ionic groups may be amphoteric systems whose properties can be varied as a function of pH. To adjust the pH of formulations based on these polymers it is possible to use the above-mentioned acids and bases. The resulting salts of the polymers usually have better solubility in water or dispersibility in water than the unneutralized polymers.

Polymers which have both cationogenic and anionogenic groups can be subjected one after the other to a neutralization with at least one acid, a neutralization with at least one base and, if desired, additionally to a quaternization. The order of the neutralization steps here is generally arbitrary. Water-soluble or water-dispersible polymers containing free cationic (amine) groups or containing free anionic (acid) groups can be reacted as "macromolecular neutralizing agent" with at least one further ionogenic polymer to give a water-dispersible or water-soluble polymeric acid-base complex. These are suitable for a wide range of cosmetic applications. Suitable polymers are described below.

The polymers used in the compositions according to the invention have K values (measured in accordance with E. Fikentscher, Cellulose-Chemie 13 (1932), page 58-64, using a 1% strength by weight solution in ethanol) in a range of from about 15 to 90, preferably from 20 to 60. Their glass transition temperature is generally at least 0° C., preferably at least 20° C., particularly preferably at least 25° C. The glass transition temperature is then typically in a range of from about 30 to 130° C., in particular from 40 to 100° C.

The polymers present in the compositions according to the invention can be used as auxiliaries in cosmetics and pharmacy, especially as or in coating compositions for keratinous surfaces (hair, skin and nails) and as coating compositions and/or binders for solid drug forms. In addition, they can be used as or in coating compositions for the textile, paper, printing, leather and adhesives industries. They are particularly suitable for use in hair cosmetics. The abovementioned polymers can also be used in creams and as tablet coatings and tablet binders. They are also suitable as binders and adhesives for cosmetic products, e.g. in the preparation of make-up, such as mascara and blusher, and in the preparation of cosmetic stick products, such as deodorant sticks, make-up sticks, etc.

The cosmetic compositions according to the invention are particularly suitable as coating compositions for keratinous surfaces (hair, skin and nails). Specifically, the polymers according to the invention and polymers used according to the invention are suitable as auxiliaries and active ingredients in hair cosmetic compositions. This includes the use as setting polymers in hairsprays and setting foams, as conditioners and thickeners in hair mousse, hair gel and shampoos. Preference is given to hair gels which, in addition to the polymers according to the invention and polymers used according to the invention, do not comprise further thickeners. The compounds used therein are water-soluble or water-dispersible. If the compounds used in the compositions according to the invention are water-dispersible, they can be used in the form of aqueous microdispersions having particle diameters of, customarily, up to 500 nm, preferably 1 to 300 nm. The solids contents in the preparations are here usually in a range of from about 0.2 to 20% by weight, preferably from 0.5 to 12% by weight. These microdispersions do not normally require emulsifiers or surfactants for stabilization.

The compositions according to the invention can preferably be in the form of a hair-treatment composition, especially in the form of a hairspray. For use as hair-setting agents, preferred compositions are those comprising polymers having at least one glass transition temperature $T_g$ of $\geq 20°$ C., preferably $\geq 30°$ C. The K value of these polymers is preferably in a range from 23 to 90, in particular from 25 to 60.

The compositions according to the invention generally comprise the polymers in an amount in the range of from 0.2 to 20% by eight, based on the total weight of the composition.

The compositions are preferably hair-treatment compositions. They are usually in the form of an aqueous dispersion or in the form of an alcoholic or aqueous-alcoholic solution. Examples of suitable alcohols are ethanol, propanol, isopropanol etc.

In addition, the hair-treatment compositions according to the invention generally comprise customary cosmetic auxiliaries, for example softening agents, such as glycerol and glycol; emollients; perfumes; UV absorbers; dyes; antistats; agents for improving combability; preservatives; waxes, especially fatty amides; and antifoams.

When formulated as hairsprays, the compositions according to the invention comprise a sufficient amount of a propellant. Preferred propellants are hydrocarbons (LPGs), in particular propane, n-butane, n-pentane and mixtures thereof. Suitable low-boiling propellants are also ethers, preferably dimethyl ether. If desired, compressed gases, such-as nitrogen, air or carbon dioxide can also be used as propellant. The above-mentioned polymers used in the compositions according to the invention have good propellant compatibility, in particular good compatibility toward hydrocarbons, and can be formulated to give products with a high propellant content of, for example, at least 40% by weight, preferably at least 50% by weight, based on the total weight of the composition. Generally, however, it is also possible to keep the propellant content low in order to formulate products with a low VOC content. In such products, the propellant content is then generally no more than 55% by weight, based on the total weight of the composition. The hair-setting compositions according to the invention are also suitable for pump-spray preparations without the addition of propellants.

The above-described polymers can also be used in combination with other hair polymers in the composition. Such polymers are, in particular:

nonionic, water-soluble or water-dispersible polymers or oligomers, such as polyvinylcaprolactam, e.g. Luviskol Plus (BASF), or polyvinylpyrrolidone and copolymers thereof, in particular with vinyl esters, such as vinyl acetate, e.g. Luviskol VA 37 (BASF); polyamides, e.g. those based on itaconic acid and aliphatic diamines;

amphoteric or zwitterionic polymers, such as the octylacrylamide/methyl methacrylate/tert-butylaminoethyl methacrylate/2-hydroxypropyl methacrylate copolymers obtainable under the names Amphomer® (Delft National), and zwitterionic polymers as disclosed, for example, in German Patent Applications DE 39 29 973, DE 21 50 557, DE 28 17 369 and DE 37 08 451. Acrylamidopropyltrimethylammonium chloride/acrylic acid or methacrylic acid copolymers and their alkali metal and ammonium salts are preferred zwitterionic polymers. Other suitable zwitterionic polymers are methacroylethylbetaine/methacrylate copolymers, which are obtainable commercially under the name Amersette® (AMERCHOL) and copolymers of hydroxyethyl methacrylate, methyl methacrylate, N,N-dimethylaminoethyl methacrylate and acrylic acid (Jordapon®);

anionic polymers, such as vinyl acetate/crotonic acid copolymers, as are available commercially, for example, under the names Resyn® (NATIONAL STARCH), Luviset® (BASF) and Gafset® (GAF), vinylpyrrolidone/vinyl acrylate copolymers, obtainable, for example, under the trade name Luviflex® (BASF). A preferred polymer is the vinylpyrrolidone/acrylate terpolymer obtainable under the name Luviflex® VBM-35 (BASF), acrylic acid/ethyl acrylate/N-tert-butylacrylamide terpolymers, which are marketed, for example, under the name Ultrahold® strong (BASF), and Luvimer® (BASF, terpolymer of tert-butyl acrylate, ethylacrylate and methacrylic acid), or cationic (quaternized) polymers, e.g. cationic polyacrylate copolymers based on N-vinyllactams and derivatives thereof (N-vinylpyrrolidone, N-vinylcaprolactam etc.) and customary cationic hair conditioning polymers, e.g. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers formed by reacting polyvinylpyrrolidone with quaternary ammonium compounds), Polymer JR (hydroxyethylcellulose with cationic groups), polyquaternium grades (CTFA names) etc.;

nonionic, siloxane-containing, water-soluble or -dispersible polymers, e.g. polyether siloxanes, such as Tegopren® (Goldschmidt) or Belsil® (Wacker).

The polymers according to the invention can be used with uncrosslinked and crosslinked siloxane-containing polyurethanes and/or with at least one other siloxane-free amide-containing hair polymer. Such polymers include, for example, the polyurethanes described in DE-A-42 25 045, the above-described vinylpyrrolidone/acrylate terpolymers and acrylic acid/ethyl acrylate/N-tert-butylacrylamide terpolymers (e.g. Ultrahold® strong from BASF AG), the cationic polyurethanes described in DE-A-42 41 118, the above-described amide-containing amphoteric polymers (e.g. Amphomer®) and, in particular, copolymers which have a content of amide-containing monomers, such as N-vinyllactams, of at least 30% by weight, (e.g. Luviskol®plus and Luviskol®VA37 from BASF AG).

The other hair polymers are preferably present in amounts of up to 10% by weight, based on the total weight of the composition.

A preferred hair-treatment composition comprises:
A) 0.2 to 20% by weight of at least one water-soluble or water-dispersible polymer, as defined in any of claims 1 to 5,
B) 30 to 99.5% by weight, preferably 40 to 99% by weight, of at least one solvent chosen from water, water-miscible solvents and mixtures thereof,
C) 0 to 70% by weight of propellant,
D) 0 to 10% by weight of at least one water-soluble or water-dispersible hair polymer which is different from A),
E) 0 to 0.3% by weight of at least one water-insoluble silicone,
F) 0 to 0.5% by weight of at least one wax, preferably at least one fatty acid amide,
and customary additives.

The composition according to the invention can comprise, as component D), at least one other water-soluble or water-dispersible hair polymer. The content of this component is then generally from about 0.1 to 10% by weight, based on the total weight of the composition. Here, it is preferable to use water-soluble or water-dispersible polyurethanes which, if desired, additionally comprise siloxane groups in copolymerized form.

The composition according to the invention can comprise, as component E), at least one water-insoluble silicone, in particular a polydimethylsiloxane, e.g. the Abil® grades from Goldschmidt. The content of this component is then generally from about 0.0001 to 0.2% by weight, preferably from 0.001 to 0.1% by weight, based on the total weight of the composition.

Preference is given to using at least one fatty acid amide, such as, for example, erucamide, as component F).

The composition according to the invention can, where appropriate, additionally comprise an antifoam, e.g. one based on silicone. The amount of antifoam is generally up to 0.001% by weight, based on the total amount of the composition.

The compositions according to the invention have the advantage that, on the one hand, they impart the desired hold to the hair and, on the other hand, the polymers are easy to wash out (redispersible). Generally, a natural appearance and shine is imparted to the hair, even when the hair is by its very nature especially thick and/or dark.

In particular, the compositions according to the invention can be formulated to give hair-treatment compositions, in particular hairsprays, with a high propellant content. Advantageously, the hair-treatment compositions according to the invention essentially do not have a "flaking" effect.

The invention is illustrated in more detail by reference to the nonlimiting examples below.

EXAMPLES

Comparative Examples A-C, Examples 1-25

Solution Polymerization (Example 13)
Feed 1: 640 g of monomer mixture of 590 g of vinylpyrrolidone and 50 g of N-[3-(dimethylamino)propyl]acrylamide (DMAPMA)
Feed 2: 350 g of monomer mixture of 250 g of tert-butyl acrylate, 50 g of N,N-dimethylaminopropylacrylamide and 50 g of stearyl methacrylate
Feed 3: 2.5 g of 2,2'-azobis(2-methylbutyronitrile) in 300 g of ethanol
Feed 4: 7.5 g of 2,5-bis(tert-butylperoxy-2,5-dimethylhexane) (Trigonox® 101 from Akzo Nobel) in 500 g of ethanol
Feed 5: 104 g of phosphoric acid (50% strength in ethanol)

A stirred apparatus fitted with reflux condenser and three separate feed devices was charged with 128 g of feed 1, 35 g of feed 2, 20 g von feed 3 and 10 g of ethoxilated polysiloxane (Belsil® DMC 6031 from Wacker) and 200 g of ethanol, and the mixture was heated to about 75° C. with stirring. After partial polymerization, recognizable when the viscosity starts to increase, the remainder of feed 1 was added over the course of an hour, the remainder of feed 2 was added over the course of four hours and the remainder of feed 3 was added over the course of five hours, the internal temperature increasing to about 80° C.

When the metered addition was complete, the mixture was afterpolymerized for a further two hours at this temperature.

To reduce the residual monomer content, feed 4 is then added over the course of two hours and the reaction mixture is afterpolymerized for 10 hours at 130° C. under autogenous pressure. (Alternatively, the residual monomer content can also be achieved by the addition of water and phosphoric acid and subsequent heating to temperatures up to 100° C., the phosphoric acid being added in an amount until a pH in the range from 4.5 to 5.5 is achieved (corresponding to a neutralization of the DMAPMA used of from 80 to 120 mol %). A steam distillation is then preferably carried out until an internal temperature of about 100° C. is reached.)

After cooling, the mixture is neutralized by the addition of feed 5 over the course of 30 minutes with stirring.

The performance properties of the resulting polymers are given in Table 3.

The ethanolic product solutions can, if desired, be admixed with water after the neutralization, and the alcohol can be removed by distillation. This gives aqueous (micro) dispersions. Pulverulent products can be obtained by spray-drying or freeze-drying.

The polymers A-C, 1-12 and 14-33 were also prepared analogously to this preparation procedure.

All of the polymers in Table 1 below have K values (measured in 1% strength ethanolic solution) in the range from 37 to 45.

TABLE 1

| Ex. No. | TBA [1] | nBA [2] | SMA [3] | LA [4] | MAA [5] | VP [6] | VFA [7] | DMA PMA [8] | Siloxane [9] | AA [10] | VI [11] |
|---|---|---|---|---|---|---|---|---|---|---|---|
| A | — | 25 | — | — | — | 65 | — | 10 *) | — | — | — |
| B | — | — | 10 | — | — | 80 | — | 10 **) | — | — | — |
| C | — | — | 30 | — | — | 60 | — | 10 **) | — | — | — |
| 1 | 10 | — | — | — | — | 80 | — | 10 **) | — | — | — |
| 2 | 25 | — | — | — | — | 65 | — | 10 *) | — | — | — |
| 3 | 30 | — | — | — | — | 60 | — | 10 **) | — | — | — |
| 4 | 15 | — | 5 | — | — | 65 | — | 15 *) | — | — | — |
| 5 | 15 | — | — | 5 | — | 64 | — | 15 *) | 1 | — | — |
| 6 | 25 | — | — | — | — | 65 | — | 10 *) | — | — | — |
| 7 | 25 | — | — | — | — | 55 | — | 20 *) | — | — | — |
| 8 | 25 | — | — | — | — | 55 | — | 17 *) | 3 | — | — |
| 9 | 25 | 10 | — | — | — | 50 | — | 15 *) | — | — | — |
| 10 | 30 | — | — | — | — | 60 | — | 10 *) | — | — | — |
| 11 | 30 | — | — | — | — | 50 | — | 20 *) | — | — | — |
| 12 | 30 | — | — | — | — | 59 | — | 10 *) | 1 | — | — |
| 13 | 25 | — | — | 5 | — | 59 | — | 10 *) | 1 | — | — |
| 14 | 40 | — | — | — | 6 | 40 | — | 12 *) | 2 | — | — |
| 15 | 40 | — | — | — | — | 50 | — | 10 *) | — | — | — |
| 16 | 40 | — | — | — | — | 50 | — | 10 **) | — | — | — |
| 17 | 40 | — | — | — | — | 49.5 | — | 10 **) | 0.5 | — | — |
| 18 | 49 | — | — | — | — | 35 | — | 15 *) | 1 | — | — |
| 19 | 49 | — | — | — | 5 | 30 | — | 15 *) | 1 | — | — |
| 20 | 30 | 19 | — | — | 5 | 27 | — | 17 *) | 2 | — | — |
| 21 | 20 | — | — | — | — | 70 | — | 10 *) | — | — | — |
| 22 | 20 | — | — | — | 4 | 65 | — | 8 *) | 3 | — | — |
| 23 | 20 | — | — | — | 3.5 | — | 70 | 6.5 *) | — | — | — |
| 24 | 30 | — | — | — | 7 | — | 50 | 13 *) | — | — | — |
| 25 | 32 | — | — | — | 8 | — | 40 | 16 *) | 4 | — | — |
| 26 | 40 | — | — | — | 5 | 38 | — | 10 | 7 | — | — |
| 27 | 40 | — | — | — | 4/3 ***) | 38 | — | 8 | 7 | — | — |
| 28 | 32 | — | 8 | — | 3/9 ***) | 35 | — | 6 | 7 | — | — |
| 29 | 30 | — | — | — | 5 | 20 | — | 10 | 5 | — | — |
| 30 | 40 | — | — | — | 4/3 ***) | 20 | — | 8 | 7 | 18 | — |
| 31 | 20 | — | — | — | 2/10 ***) | 20 | — | 4 | 4 | 40 | — |
| 32 | 20 | — | — | — | 5 | 20 | — | 10 | 4.5 | — | — |
| 33 | 10 | — | — | — | 9 | 60 | — | — | — | 70.7 | 10 |

*) neutralized with $H_3PO_4$, degree of neutralization about 90%
**) instead of the addition of phosphoric acid, the copolymerized DMAPMA was quaternized by the addition of from 0.9 to 1 equivalent of diethyl sulfate, based on DMAPMA, at 40° C. (about 1 h).
***) not neutralized/neutralized with KOH

[1] TBA = tert-butyl acrylate
[2] nBA = n-butyl acrylate
[3] SMA = stearyl methacrylate
[4] LA = lauryl acrylate
[5] MAA = methacrylic acid
[6] VP = N-vinylpyrrolidone
[7] VFA = N-vinylformamide
[8] DMAPMA = N-[3-(dimethylamino)propyl]acrylamide
[9] Siloxane = ethoxylated polysiloxane (Belsil ® DMC 6031 from Wacker)
[10] AA = acrylamide
[11] VI = vinylimidazole Performance Properties For the polymers from Comparative Examples A-C and Examples 1-25 according to the invention, the n-heptane compatibility was determined as a measure of their propellant compatibility. For this, 1.5 g of each neutralized polymer and 23.5 g of ethanol were formulated to give 6% strength by weight solutions, which were titrated at room temperature (22° C.) with n-heptane until turbidity appeared. The percentate n-heptane compatibility was converted to a scale of grades as in Table 2.

The polymers from Comparative Examples A-C and from Examples 1-25 according to the invention were formulated to give 5% strength by weight ethanolic solutions. They were applied to a glass plate, and the resulting films were tested by five experts with regard to three criteria (ability to be washed out, tackiness and feel), which are given in Table 2, and were graded from 1 to 4. The gradings for the films are given in Table 3. The strength of the hold was evaluated using a dummy head.

TABLE 2

| Grade | Heptane compati-bility | Hold | Ability to be washed out | Tackiness | Feel |
|---|---|---|---|---|---|
| 1 | >65% | very good | very good | nontacky | very soft |
| 2 | 50-65% | good | good | slightly tacky | good, soft |
| 3 | 35-50% | moderate | moderate | tacky | rough, harsh |
| 4 | <35% | poor | poorly soluble | very tacky | rough, inhibitory, unnatural |

TABLE 3

| | Grade | | | | |
|---|---|---|---|---|---|
| Ex. No. | Heptane compati-bility | Hold | Ability to be washed out | Tackiness | Feel |
| A | 2 | 2 | 1-2 | 2 | 2-3 |
| B | 1 | 2 | 1-2 | 2 | 3 |
| C | 1 | 2-3 | 3 | 2-3 | 3 |
| 1 | 1 | 1-2 | 1 | 2 | 1-2 |
| 2 | 1 | 1-2 | 1-2 | 1-2 | 2 |
| 3 | 1 | 1 | 1 | 1-2 | 2 |
| 4 | 1 | 1 | 1-2 | 1-2 | 2 |
| 5 | 1 | 1-2 | 1-2 | 1-2 | 1-2 |
| 6 | 1 | 1 | 1 | 1-2 | 2 |
| 7 | 2 | 1 | 1 | 1-2 | 2 |
| 8 | 1-2 | 1-2 | 1 | 1-2 | 1-2 |
| 9 | 1 | 1-2 | 1 | 1-2 | 2 |
| 10 | 1 | 1 | 1 | 1-2 | 2 |
| 11 | 1-2 | 1 | 1 | 1 | 2 |
| 12 | 1 | 1 | 1 | 1-2 | 1-2 |
| 13 | 1 | 1 | 1 | 1-2 | 1-2 |
| 14 | 1 | 1 | 1 | 1 | 1-2 |
| 15 | 1 | 1 | 1-2 | 1 | 2 |
| 16 | 1 | 1 | 1 | 1-2 | 1-2 |
| 17 | 1 | 1 | 1 | 1-2 | 1-2 |
| 18 | 1 | 1 | 1 | 1 | 1-2 |
| 19 | 1 | 1 | 1 | 1 | 1-2 |
| 20 | 1-2 | 1-2 | 1 | 1-2 | 1 |
| 21 | 1-2 | 2 | 1 | 2 | 2 |
| 22 | 1-2 | 2 | 1 | 1-2 | 1-2 |
| 23 | 2 | 2*) | 1 | 2 | 1-2 |
| 24 | 1-2 | 1-2*) | 1 | 1-2 | 1-2 |
| 25 | 1-2 | 1-2*) | 1 | 1-2 | 1 |

*)measured on a film of a hairspray formulation with a VOC content of 80% by weight (propellant gas: dimethyl ether)

Examples 26 to 50

Aerosol hairspray formulations with a VOC content of 95% by weight:

| | |
|---|---|
| Polymer as in Ex. 1-25 | 5.00% by weight |
| Ethanol | 55.00% by weight |
| Propane/butane | 39.96% by weight |
| Perfum, additives | q.s. |

Examples 51 to 75

Aerosol hairspray formulations with a VOC content of 95% by weight:

| | |
|---|---|
| Polymer as in Ex. 1-25 | 5.00% by weight |
| Ethanol | 40.00% by weight |
| Propane/butane | 54.96% by weight |
| Perfume, additives | q.s. |

Examples 76 to 100

Compact aerosol hairspray formulations with a VOC content of 80% by weight:

| | |
|---|---|
| Polymer as in Ex. 1-25 | 5.00% by weight |
| Ethanol | 40.00% by weight |
| Dimethyl ether | 39.96% by weight |
| Water | 15.00% by weight |
| Perfume, additives | q.s. |

Examples 101 to 117 hairspray formulations with a VOC content of 55% by weight:

| | |
|---|---|
| Polymer as in Ex. 1-3, 7-14, 16-21 | 3.00% by weight |
| Ethanol | 15.00% by weight |
| Water | 42.00% by weight |
| Dimethyl ether | 39.96% by weight |
| Perfume, additives | q.s. |

Examples 118 to 142

Pump Hairspray:

| | |
|---|---|
| Polymer as in Ex. 1-25 | 5.00% by weight |
| Ethanol | 94.96% by weight |
| Perfume, additives | q.s. |

Examples 143 to 167

Pump Hairspray:

| | |
|---|---|
| Polymer as in Ex. 1-25 | 5.00% by weight |
| Ethanol | 79.96% by weight |

Examples 168 to 192

| Foam conditioner | [% by weight] |
| --- | --- |
| Polymer 1-25 (20% strength aqueous solution) | 30.00 |
| Cremophor ® A25[8] | 0.20 |
| Comperlan ® KD[9] | 0.10 |
| Water | 59.70 |
| Propane/butane | 9.96 |
| Perfume, preservative | q.s. |

[8] CTFA name: Ceteareth 25, BASF AG, reaction product of fatty alcohol and ethylene oxide
[9] CTFA-Name: Cocamide DEA, Henkel, coconut fatty acid amide To prepare the foam conditioners, the components are weighed in and dissolved with stirring. They are then transferred to a dispenser, and propellant is added.

Examples 193 to 217

Hair-Setting Gel
Phase I:

| | |
| --- | --- |
| Polymer 1-25 (20% strength aqueous solution) | 25.00% by weight |
| Polysorbate 20 | 1.00% by weight |
| Imidazolidinylurea | 0.10% by weight |
| Perfum, additives | q.s. |

Phase II:

| | |
| --- | --- |
| Hydroxyethylcellulose | 1.40% by weight |
| Ethoxylated oleyl alcohol (20 EO) | 0.10% by weight |
| Water | 72.36% by weight |

Examples of Applications in Hair Cosmetics

Examples 218 to 242

O/W Creams

| | % by wt. | CTFA name: |
| --- | --- | --- |
| Oil phase: | | |
| Cremophor ® A6 (BASF AG) | 3.5 | ceteareth-6 (stearyl alcohol ethoxylate) |
| Cremophor ® A25 (BASF AG) | 2.5 | ceteareth-25 (fatty alcohol ethoxylate) |
| Glycerol monostearate s. e. | 2.5 | Glyceryl stearate |
| Paraffin oil | 7.5 | |
| Cetyl alcohol | 2.5 | |
| Luvitol ® EHO (BASF AG) | 3.2 | Cetearyl octanoate |
| Vitamin E acetate | 1.0 | |
| Nip-Nip ®, Nipa Laboratories Ltd., USA | 0.1 | Methyl and propyl 4-hydroxybenzoates (7:3) |
| Water Phase | | |

| | % by wt. | CTFA name: |
| --- | --- | --- |
| Polymer 1-25 | 1.5 | |
| Water | 73.6 | |
| Germall II, Sutton Laboratories Inc., USA | 0.1 | Imidazolidinylurea |
| 1,2-Propylene glycol | 1.0 | |

To prepare the creams, the components for the oil and water phase are weighed in separately and homogenized at 80° C. The water phase is then slowly added to the oil phase with stirring. The mixture is then left to cool to room temperature with stirring.

Examples 243 to 267

O/W Creams

| | % by wt. | CTFA name: |
| --- | --- | --- |
| Oil phase: | | |
| Cremophor ® A6 (BASF AG) | 2.0 | Ceteareth-6 (stearyl alcohol ethoxylate) |
| Cremophor ® A25 (BASF AG) | 2.0 | Ceteareth-25 (fatty alcohol ethoxylate) |
| Glycerol monostearate s. e. | 6.0 | Glyceryl stearate |
| Paraffin oil | 0.9 | |
| Tegiloxan 100 | 0.1 | Dimethicone |
| Cetyl alcohol | 1.5 | |
| Luvitol ® EHO (BASF AG) | 12.0 | Cetearyl octanoate |
| Vitamin E acetate | 0.4 | |
| Water phase: | | |
| Polymer 1-25 | 1.0 | |
| Water | 74.6 | |
| 1,2-Propylene glycol | 1.0 | |
| Germall II, Sutton Laboratories Inc., USA | 0.1 | Imidazolidinylurea |

To prepare the creams, the components for the oil and water phase are weighed in separately and homogenized at 80° C. The water phase is then slowly added to the oil phase with stirring. The mixture is then left to cool to room temperature with stirring.

Examples for use as hair-setting polymer in hair cosmetics

Examples 268-277

| VOC 80 aerosol hairspray | [% by wt.] |
| --- | --- |
| Polymer 14/19/20/22/25/26-30 | 4.00 |
| Luviset ® PUR (polyurethane hair polymer from BASF) | 1.00 |
| Water | 15.00 |
| Dimethyl ether | 40.00 |
| Ethanol | 40.00 |
| Silicone, perfume, antifoam | q.s. |

Examples 278-287

| VOC 80 aerosol hair spray | [% by wt.] |
|---|---|
| Polymer 14/19/20/22/25/26-30 | 1.50 |
| Luviset PUR | 3.50 |
| Water | 15.00 |
| Dimethyl ether | 40.00 |
| Ethanol | 40.00 |
| Silicone, perfume, antifoam | q.s. |

Examples 288-297

| VOC 55 aerosol hairspray | [% by wt.] |
|---|---|
| Polymer 14/19/20/22/25/26-30 | 1.00 |
| Luviset PUR | 2.00 |
| Water | 42.00 |
| Dimethyl ether | 35.00 |
| Ethanol | 20.00 |
| Silicone, perfume, antifoam | q.s. |

Examples 298-307

| VOC 55 hand pump spray | [% by wt.] |
|---|---|
| Polymer 14/19/20/22/25/26-30 | 1.50 |
| Luviset PUR | 3.50 |
| Water | 40.00 |
| Ethanol | 55.00 |
| Silicone, perfume, antifoam | q.s. |

Examples 308-312

| Foam conditioner | [% by wt.] |
|---|---|
| Polymer 26-30 (25% strength aqueous solution) | 20.00 |
| Cremophor ® A25 (Ceteareth-25/BASF) | 0.20 |
| Comperlan ® KD (Cocamide DEA/Henkel) | 0.10 |
| Water | 69.70 |
| Propane/butane | 10.00 |
| Silicone, perfume, preservative | q.s. |

Preparation: The components are weighed in, dissolved with stirring and containerized and then the propellant gas is added.

Examples 313-315

| Conditioner shampoo | [% by wt.] |
|---|---|
| Polymer 26-30 (25% aqueous solution) | 20.00 |
| A) Texapon ® NSO 28% strength (sodium lauryl sulfate/Henkel) | 50.00 |
| Comperlan ® KD (Cocamide DEA/Henkel) | 1.00 |
| Polymer 31-33 (25% aqueous solution) | 20.00 |
| Perfume oil | q.s. |
| B) Water | 27.50 |
| Sodium chloride | 1.50 |
| Preservative etc. | q.s. |

Preparation: The components are weighed in, phases A and B are dissolved separately with stirring and mixed. Phase B is then slowly stirred into phase A.

Use in Skin Cosmetics

Examples 316-328

Standard O/W Creams

|  | % by wt. | CTFA name: |
|---|---|---|
| Oil phase: | | |
| Cremophor ® A6 (BASF AG) | 3.5 | Ceteareth-6 (and) stearyl alcohol |
| Cremophor ® A25 (BASF AG) | 3.5 | Ceteareth-25 |
| Glycerol monostearate s. e. | 2.5 | Glyceryl stearate |
| Paraffin oil | 7.5 | |
| Cetyl alcohol | 2.5 | |
| Luvitol ® EHO (BASF AG) | 3.2 | Cetearyl octanoate |
| Vitamin E acetate | 1.0 | Tocopheryl acetate |
| NiP-NiP ®, Nipa Lab. Ltd., USA | 0.1 | Methyl and propyl 4-hydroxybenzoate (7:3) |
| Water phase: | | |
| Polymer 14/19/20/22/25/26-33 | 1.5 | |
| Water | 73.6 | |
| 1,2-Propylene glycol | 1.0 | |
| Germall II, Sutton Lab. Inc., USA | 0.1 | Imidazolidinylurea |

To prepare the creams, the components for the oil and water phases are weighed in separately and homogenized at 80° C. The water phase is then slowly added to the oil phase with stirring. The mixture is then left to cool to room temperature with stirring.

We claim:

1. A cosmetic composition comprising at least one water-soluble or water-dispersible polymer which comprises, in incorporated form, a) 7 to 45% by weight of at least one α,β-ethylenically unsaturated monomer of the formula I

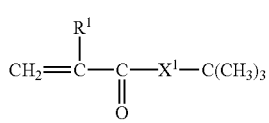

in which
$R^1$ is hydrogen or $C_1$- to $C_8$-alkyl, and
$X^1$ is O, b) 25 to 90% by weight of at least one N-vinylamide and/or N-vinyllactam, c) 0.5 to 30% by weight of at least one compound having a free-radically polymerizable, α,β-ethylenically unsaturated double bond and at least one cationogenic and/or cationic group per molecule, wherein the cationic and cationogenic groups are selected from optionally protonated primary, secondary and tertiary amino groups and quaternized ammonium groups;

d) 0 to 30% by weight of at least one α,β-ethylenically unsaturated monomer selected from the group consisting of methacrylic acid and monomers of the formula II

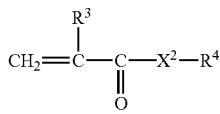

(II)

in which
$R^3$ is hydrogen or $C_1$- to $C_8$-alkyl,
$X^2$ is O or $NR^5$, where $R^5$ is hydrogen $C_1$- to $C_8$-alkyl or $C_5$- to $C_8$-cycloalkyl, and
$R^4$ is a linear $C_1$- to $C_{22}$-alkyl radical,
or the salts thereof;

wherein the polymer does not comprise, in incorporated form, monomers having at least two ethylenically unsaturated nonconjugated double bonds;

and wherein components c), d) and optionally a component e) are present in amounts such that the ratio of equivalents of the cationogenic groups is greater than or equal to the equivalents of anionogenic groups;

and a customary cosmetic auxiliary.

2. A composition as claimed in claim 1, where the water-soluble or water-dispersible polymer comprises, in copolymerized form, methacrylic acid in an amount of from 0.1 to 20% by weight, based on the total amount of the monomers a), b), c) and d).

3. A composition as claimed in claim 1, where the polymer comprises, in copolymerized form, at least one further component chosen from
e) compounds different from acrylic acid and the monomers defined in component d), having a free-radically polymerizable α,β-ethylenically unsaturated double bond and at least one anionogenic and/or anionic group per molecule,
g) free-radically polymerizable monomers different from a) to e), and mixtures thereof.

4. A composition as claimed in claim 1, wherein the polymer comprises the compounds of components d) and e), wherein e) comprises compounds different from
d) having a free-radically polymerizable α,β-ethylenically unsaturated double bond and at least one anionogenic and/or anionic group per molecule, containing at least one anionogenic and/or anionic group per molecule in an amount of from 0.1 to 15% by weight, based on the total weight of the monomers to be polymerized, in copolymerized form.

5. A composition as claimed in claim 1, wherein the polymer comprises
7 to 45% by weight of at least one component a),
30 to 87% by weight of at least one component b),
1 to 25% by weight of at least one component c),
0.1 to 25% by weight of at least one component d), and, optionally,
0 to 15% by weight of at least one component e) in copolymerized form.

6. A composition as claimed in claim 1, which additionally comprises at least one polysiloxane which contains polyalkylene oxide groups.

7. A composition as claimed in claim 6, where the polysiloxane is chosen from compounds of the formula III

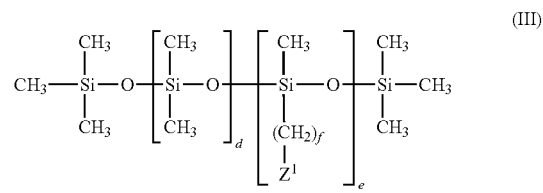

(III)

in which the order of the siloxane units is arbitrary,
d and e, independently of one another, are 0 to 100, where the sum d+e is at least 2,
f is an integer from 2 to 5,
$Z^1$ is a radical of the formula IV

(IV)

where in the formula IV the order of the alkylene oxide units is arbitrary,
u is an integer from 1 to 8,
v and w, independently of one another, are an integer from 0 to 200, where the sum v+w is >0, and
$R^A$ is hydrogen or $C_1$-$C_6$-alkyl.

8. A composition as claimed in claim 6, where the quantitative ratio of water-soluble or water-dispersible polymer to polysiloxane is in a range from 70:30 to 99.9:0.1.

9. A composition as claimed in claim 6, where the water-soluble or water-dispersible polymer used is a polymer obtained by free-radical polymerization of the monomers forming the polymer in the, presence of at least one polysiloxane which contains polyalkylene oxide groups.

10. A composition as claimed in claim 1 in the form of a hair-treatment composition.

11. A composition as claimed in claim 10, wherein the polymer is used in combination with other hair polymers, selected from
nonionic, water-soluble or water-dispersible polymers or oligomers,
amphoteric or zwitterionic polymers,
anionic polymers,
cationic polymers, and
nonionic, siloxane-containing, water-soluble or water-dispersible polymers.

12. A composition as claimed in claim 10, comprising
A) 0.2 to 20% by weight of the at least one water-soluble or water-dispersible polymer,
B) 30 to 99.5% by weight of at least one solvent chosen from water, water-miscible solvents and mixtures thereof,
C) 0 to 70% by weight of propellant,
D) 0 to 10% by weight of at least one water-soluble or water-dispersible hair polymer which is different from A),
E) 0 to 0.3% by weight of at least one water-insoluble silicone,
F) 0 to 0.5% by weight of at least one wax.

13. A composition as claimed in claim 12, wherein as component D) at least one water-soluble or water-dispersible polyurethane is used with or without siloxane groups in copolymerized form.

14. A water-soluble or water-dispersible polymer which comprises, in copolymerized form,
a) 7 to 45% by weight of at least one α,β-ethylenically unsaturated monomer of the formula I

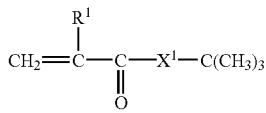

in which
R¹ is hydrogen or $C_1$- to $C_5$-alkyl, and
X¹ is O,
b) 25 to 90% by weight of at least one N-vinylamide and/or N-vinyllactam,
c) 0.5 to 30% by weight of at least one compound having a free-radically polymerizable, α,β-ethylenically unsaturated double bond and at least one cationogenic and/or cationic group per molecule, wherein the cationogenic groups are selected from optionally protonated primary, secondary and tertiary amino groups and quaternized ammonium groups;
d) 0.1 to 30% by weight of at least one α,β-ethylenically unsaturated monomer selected from the group consisting of methacrylic acid and monomers of the formula II

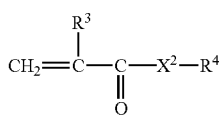

in which
R³ is hydrogen or $C_1$- to $C_8$-alkyl,
X² is O or NR⁵, in which R⁵ is hydrogen $C_1$- to $C_8$-alkyl or $C_5$- to $C_8$-cycloalkyl, and
R⁴ is a linear $C_1$- to $C_{22}$-alkyl radical;
wherein the polymer does not comprise, in incorporated form, monomers having at least two ethylenically unsaturated nonconjugated double bonds;
and wherein components c), d) and optionally a component e) are present in amounts such that the ratio of equivalents of the cationogenic groups is greater than or equal to the equivalents of anionogenic groups.

15. A polymer as claimed in claim 14 which comprises, in copolymerized form, at least one further component chosen from
e) compounds different from acrylic acid and the monomers defined in component d), having a free-radically polymerizable α,β-ethylenically unsaturated double bond and at least one anionogenic and/or anionic group per molecule,
g) free-radically polymerizable monomers different from a) to e), and mixtures thereof.

16. A polymer as claimed in claim 14 which comprises, in copolymerized form, 0.1 to 20% by weight of methacrylic acid, based on the total amount of monomers a), b), c) and d).

17. A polymer as claimed in claim 14, which comprises, in copolymerized form
a) 7 to 45% by weight of at least one monomer of the formula I,
b) 25 to 70% by weight of at least one N-vinylamide and/or N-vinyllactam,
c1) 1 to 10% by weight of methacrylic acid,
c2) 0 to 25% by weight of one or more compounds of the formula II,
e) 3 to 20% by weight of at least one compound which is different from (meth)acrylic acid and which has a free-radically polymerizable, α,β-ethylenically unsaturated double bond and at least one cationic and/or cationogenic group per molecule, and
g) 1 to 20% by weight of at least one polysiloxane which contains polyalkylene oxide groups,
where the weight fractions add up to 100% by weight.

18. A method for improving the appearance or feel of human hair, skin or nails, said method comprising applying the cosmetic formulation of claim 1 to the hair, skin or nails.

19. A composition as claimed in claim 1, where the polymer comprises, in copolymerized form, at least one further component chosen from
e) compounds different from acrylic acid and the monomers defined in component d), having a free-radically polymerizable α,β-ethylenically unsaturated double bond and at least one anionogenic and/or anionic group per molecule, and mixtures thereof 20. A polymer as claimed in claim 14 which comprises, in copolymerized form, at least one further component chosen from
e) compounds different from acrylic acid and the monomers defined in component d), having a free-radically polymerizable α,β-ethylenically unsaturated double bond and at least one anionogenic and/or anionic group per molecule, and mixtures thereof.

21. A polymer as claimed in claim 14, wherein the polymer comprises, in copolymerized form, N[3-(dimethylamino)propyl]methacrylamide and methacrylic acid in a weight ratio of from 2:0.9 to 2:1.1.

22. A polymer as claimed in claim 21, wherein the polymer does not comprise, in incorporated form, vinylcaprolactam.

23. A polymer as claimed in claim 14, wherein the N-vinylamide and/or N-vinyllactam (b) is vinylpyrrolidone and/or vinylformamide, and the polymer comprises, in copolymerized form, N[3-(dimethylamino)propyl]methacrylamide and methacrylic acid in a weight ratio of from 2:0.9 to 2:1.1.

24. A polymer as claimed in claim 14, wherein R⁴ is methyl, ethyl, n-propyl, n-butyl, n-pentyl, n-hexyl, n-heptyl or n-octyl, and the polymer comprises, in copolymerized form, N-[3-(dimethylamino)propyl]methacrylamide and methacrylic acid in a weight ratio of from 2:0.9 to 2:1.1.

25. A composition as claimed in claim 1, wherein the polymer consists of components a), b), c), and optionally d), in copolymerized form, wherein components c) and d) are present in amounts such that the ratio of equivalents of the cationogenic groups is greater than or equal to the equivalents of anionogenic groups.

26. A polymer as claimed in claim 14 which consists of components a), b), c), and d), in copolymerized form, wherein components c) and d) are present in amounts such that the ratio of equivalents of the cationogenic groups is greater than or equal to the equivalents of anionogenic groups.

* * * * *

UNITED STATES PATENT AND TRADEMARK OFFICE
CERTIFICATE OF CORRECTION

PATENT NO.      : 8,398,963 B2
APPLICATION NO. : 10/204346
DATED           : March 19, 2013
INVENTOR(S)     : Kim et al.

It is certified that error appears in the above-identified patent and that said Letters Patent is hereby corrected as shown below:

In the Claims:

Col. 26, Line 64, Claim 1

"$R^1$ is hydrogen" should read -- $R^3$ is hydrogen --

Col. 28, Line 24, Claim 7

"—$(CH_2)_u$—O—$(CH_2CH_2O)_w(CH_2CH(CH_3)O)_w$—$R^4$" should read
-- -$(CH_2)_u$-O-$(CH_2CH_2O)_v(CH_2CH(CH_3)O)_w$-$R^A$ --

Col. 29, Line 14, Claim 14

"$R^1$ is hydrogen" should read --$R^3$ is hydrogen --

Signed and Sealed this
Twenty-first Day of May, 2013

Teresa Stanek Rea
*Acting Director of the United States Patent and Trademark Office*